US00PP08359P

United States Patent [19]

Cole

[11] Patent Number: Plant 8,359

[45] Date of Patent: Aug. 31, 1993

[54] IMPATIENS PLANT NAMED PURPLE MAGIC

[76] Inventor: Douglas S. Cole, R.F.D. 13, Box 240, Concord, N.H. 03301

[21] Appl. No.: 765,053

[22] Filed: Sep. 24, 1991

[51] Int. Cl.[5] ..... A01H 5/00

[52] U.S. Cl. ..... Plt./87.6

[58] Field of Search ..... Plt./87.6, 68.0, 68.1

*Primary Examiner*—James R. Feyrer
*Assistant Examiner*—Erich Veitenheimer
*Attorney, Agent, or Firm*—Foley & Lardner

[57] ABSTRACT

A new cultivar of *Impatiens sultanii* plant named Purple Magic, characterized by its intense red-purple flower color, fully double consistent flowers, smooth, rich green foliage, compact growth habit with good branching, and its floriferous habit.

2 Drawing Sheets

1

The present invention comprises a new and distinctive cultivar of Impatiens plant, botanically known as *Impatiens sultanii*, and known by the cultivar name Purple Magic. The species name appears to be synonymous with the species designation *Impatiens wallerana*, also referred to in botanical literature.

The new cultivar is a sport or mutation of the cultivar Rosebud TM Lavender, and was discovered by me in approximately March 1990 in greenhouses in Concord, N.H. The mutation was discovered growing among plants of the parent cultivar, and was noted due to its distinctly different flower color. Subsequent asexual reproduction by stem cuttings taken by the inventor in Concord, N.H. has shown that the unique features of this new cultivar are stabilized and are reproduced true to type in successive propagations.

The following characteristics taken in combination distinguish the new cultivar Purple Magic from both its parent and other cultivated *Impatiens sultanii* of this type known and used in the floriculture industry:

1. Fully double, consistent blooms.
2. Even growing, compact, well shaped, mounded plant habit. Good self-branching if propagated from a vegetative cutting.
3. Rooting time is approximately seven days to initiate roots at 70° F.; saleable cuttings are available in 21 days at 70° F.
4. Produces cuttings very well. The highest quality cuttings are produced by removing from an approximately 3" stem and leaf cutting a ¼"-½' tip and discarding it. The remaining cutting then branches much better.
5. The foliage is smooth and rich green in color.
6. The plant flowers in approximately six weeks from a pinched rooted cutting.
7. When left to reach full bloom, the plant is coveredd with blossoms which are an intense red-purple in color.

The new cultivar is similar in most respects to the parent cultivar Rosebud TM Lavender. The primary difference is in flower color, with mature flowers of Rosebud TM Lavender having an upper surface color of red/purple 68 B-C and a lower surface color of red-purple 68 D. The mature flower color of Purple Magic is a much darker, more intense red-purple, as evidenced by the color values noted below. The foliage color of Purple Magic is slightly darker than the foliage color (137 A) of Rosebud TM Lavender, although this is not clearly shown in the photographic drawings.

2

The new cultivar can also be compared with Rosebud TM Purple, which has a similar flower color. However, Purple Magic is distinguished from Rosebud TM Purple by its richer green foliage, more compact growth habit with better branching, more resistance to yellowing of leaves, and its better vegetative growth that provides better cutting production.

The accompanying colored photographs illustrate the overall appearance of the new cultivar, showing the colors as true as it is reasonably possible to obtain in a colored reproduction of this type. The top photograph on Sheet 1 is a top perspective view of a fully grown potted plant of Purple Magic. The bottom photograph on Sheet 1 is a closeup view showing a few partially and fully open flowers. The photograph on Sheet 2 is a comparison view of mature potted plants of Rosebud TM Lavender (on left) and Purple Magic (on right).

The following is a detailed description of my new Impatiens cultivar based on plants produced under commercial practice at London, N.H. Color references are made to The Royal Horticultural Society Colour Chart except where general terms of ordinary dictionary significance are used. The color values were determined during sunny conditions at approximately 1:00 p.m. under part natural and part inflorescent light in Alexandria, Va.

Parentage: Sport of *Impatiens sultanii*, c.v. Rosebud TM Lavender.

Propagation:

A. *Type cutting.*—Stem and leaves, with the tip preferably being removed to enhance branching.

B. *Time to initiate roots.*—7 days at 21° C. summer; 7 days at 21° C. winter.

C. *Rooting habit.*—Good; roots at nodes or internodes; no hormones needed.

Plant description:

A. *Form.*—Mounded form, with some spreading and slight hanging when given space.

B. *Habit of growth.*—Compact, dense growth with excellent branching; excellent vegetative growth results in good cutting production growth is slightly slower than comparable cultivars; typical size plant grown in pot in spring programs is approximately 6-7" tall and 7-8" in diameter eight (8) weeks after planting, based on pinched, well-rooted 2" cutting.

C. *Foliage.*—1. Size (mature leaf): Width: 1" to 1¼". Length: 1½" to 2" (excluding petiole). 2. Shape: Ovate, tip acuminate, generally flat. 3. Texture: Smooth with some wrinkling. 4. Margin: Slightly serrated. 5. Color: Top side 147A, with no variegation at edges or midrib; underside, 147B-C. 6. Venation: Not distinctive.

Flowering description:

A. *Flowering habits.*—Flowers start as a bud the shape of a round ball and the size of a pea, and open similar to a rose in fulliness. The flowers open slightly above or even with the foliage. Flowering is up to one week earlier than comparable cultivars, flowering in 4–6 weeks after potting a pinched, well-rooted 2" cutting.

B. *Flowering season.*—Year-round in greenhouse environment; best in spring.

C. *Flower buds.*—Basically white with a slight touch of green; red-purple color comes out as soon as bud opens there are up to 5 buds per axil, usually 3, with the terminal bud opening first.

D. *Quantity of flowers.*—Very floriferous.

E. *Petals.*—Overall inflorescence has an almost rose or camellia type character due to fully double form. 1. Shape: Petals round to slightly oblong with indentation in tip. 2. Color: Upper surface: 74A; color retention is very good. Lower surface: 74C-D. 3. Number of petals: Multiple, twenty-five or even more. 4. Size of flowers: 1¼" to 2" in diameter.

F. *Reproductive organs.*—1. Stamens: Multiple in number; pollen color yellow. 2. Pistils: Stigma color yellow; styles and ovaries not distinctive.

G. *Fragrance.*—None.

H. *Spur.*—One per flower; attached near base, approximately 20 mm in length and curved; light green 144 A-B immature to generally transparent (no corresponding color value) when mature, with red-purple tip.

Disease resistance: Some resistance to Botrytis. Root fungi are seldom a problem

I claim:

1. A new and distinct cultivar of *Impatiens sultanii* plant named Purple Magic, as illustrated and described.

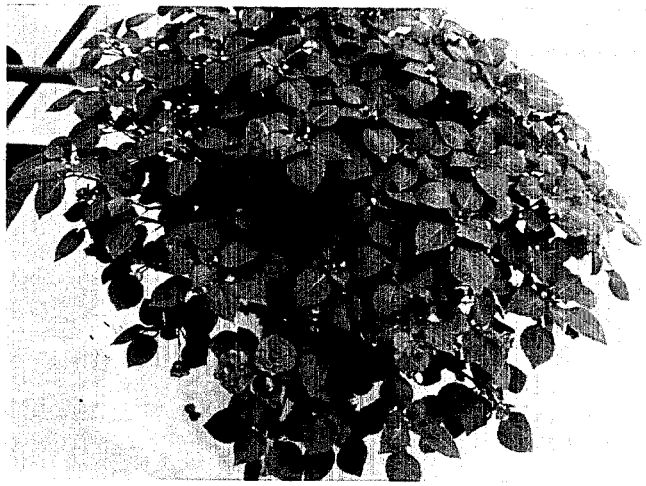
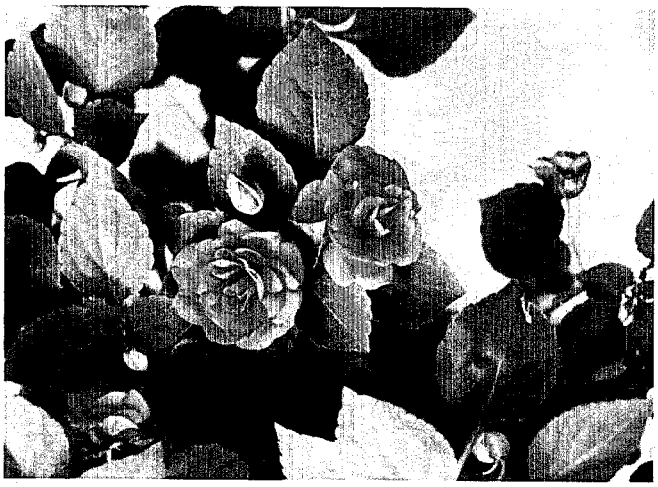

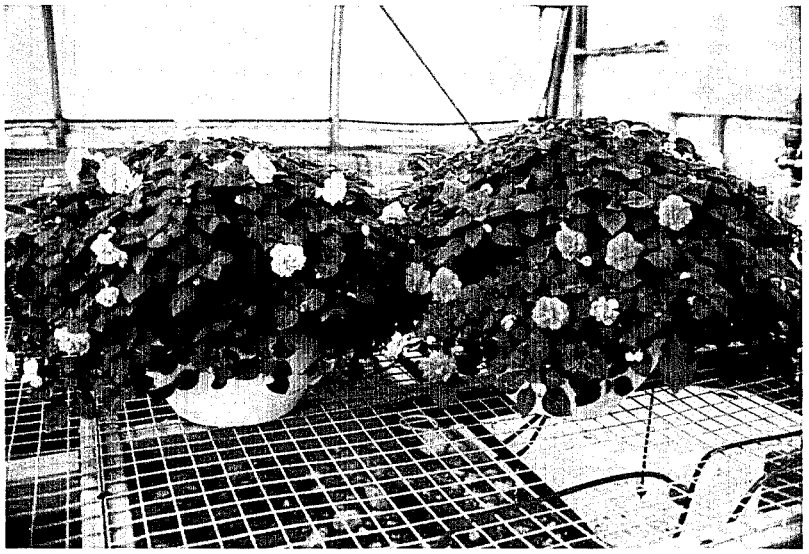

* * * * *